United States Patent [19]

Imwinkelried et al.

[11] Patent Number: 5,395,963
[45] Date of Patent: Mar. 7, 1995

[54] PROCESS FOR CHLORONITROACETIC ACID ESTERS

[75] Inventors: René Imwinkelried, Brig-Glis; Felix Previdoli, Brig, both of Switzerland

[73] Assignee: Lonza Ltd., Gampel/Valais, Switzerland

[21] Appl. No.: 118,325

[22] Filed: Sep. 9, 1993

Related U.S. Application Data

[62] Division of Ser. No. 57,639, May 7, 1993, Pat. No. 5,284,960.

[30] Foreign Application Priority Data

May 13, 1992 [CH] Switzerland ............ 1528/92

[51] Int. Cl.$^6$ .................................. C07D 209/34
[52] U.S. Cl. ............................................. 562/934
[58] Field of Search ............................. 562/434

[56] References Cited

U.S. PATENT DOCUMENTS

| | | | |
|---|---|---|---|
| 3,882,236 | 5/1975 | Molloy | 548/486 |
| 4,060,626 | 11/1977 | Hrstka et al. | 562/434 |
| 4,160,032 | 7/1979 | Hardtmann | 514/418 |
| 4,476,315 | 10/1984 | Stahly et al. | 562/434 |
| 4,659,862 | 4/1987 | Rjanbabu | 560/20 |
| 4,721,712 | 1/1988 | Kadin | 514/253 |
| 4,730,004 | 3/1988 | Kadin | 514/418 |
| 4,761,485 | 8/1988 | Marfat | 548/486 |

OTHER PUBLICATIONS

Chemical Abstracts, 89(17):146079s, (1978), p. 540.
Chemical Abstracts, 107(11):96444z, (1987), p. 664.
RajanBabu et al., J. Org. Chem., vol. 51, (1986), pp. 1704–1712.
Quallich et al., Synthesis, vol. 1, No. 93, (Jan. 1993), pp. 51–54.

*Primary Examiner*—Donald G. Daus
*Attorney, Agent, or Firm*—Fisher, Christen & Sabol

[57] ABSTRACT

A process for the production of 5-chloroxindole starting from chloronitrobenzene. In this way, in a first step, chloronitrobenzene of the formula:

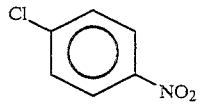

II is converted with a chloro acetic acid alkyl ester of the general formula:

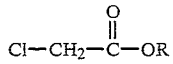

III in the presence of a base to a chloronitrobenzene acetic acid alkyl ester of the general formula:

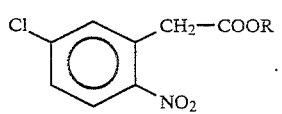

IV

The latter is catalytically hydrogenated in a second step with hydrogen to the corresponding amine of the general formula:

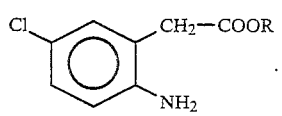

V

The latter is then cyclized in a third step in the presence of an acid to the end product according to the formula:

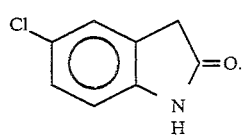

I

6 Claims, No Drawings

PROCESS FOR CHLORONITROACETIC ACID ESTERS

This is a divisional application of Ser. No. 08/057,639, filed May 7, 1993, now U.S. Pat. No. 5,284,960.

BACKGROUND OF THE INVENTION

1. Field of the Invention

The invention relates to a process for the production of 5-chloroxindole of the formula:

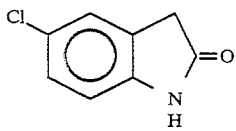

starting from chloronitrobenzene.

2. Background Art

To date several processes for the production of 5-chloroxindole are known. For example, U.S. Pat. No. 4,761,485 describes a process for the production of 5-chloroxindole starting from 5-chloroindole. In this case, 5-chloroindole is first converted by pyridinebromide perbromide into 3,3-dibromo-5-chloroxindole, which is then converted into 5-chloroxindole by catalytic hydrogenation with palladium on carbon. Drawbacks of this process are that feedstock (5-chloroindole) is difficult to obtain and that the 5-chloroindole is obtained in poor yield.

Also, U.S. Pat. No. 4,730,004 describes a process for the production of 5-chloroxindole starting from 5-chloroisatin, whereby the latter is first converted with hydrazine hydrate into the 5-chloro-3-hydrazon-2-oxoindole, which is then reacted by sodium methanolate into 5-chloroxindole. This process also has the drawbacks that the feedstock 5-chloroisatin is difficult to obtain and that the desired product is obtained in poor yield.

BROAD DESCRIPTION OF THE INVENTION

The main object of the invention is to provide an economical and simple process for the production of 5-chloroxindole with the product being obtained in a good yield. Other objects and advantages of the invention are set out herein or are obvious herefrom to one skilled in the art.

The objects and advantages are achieved by the new process according to the invention.

The invention involved a process for the production of 5-chloroxindole of the formula:

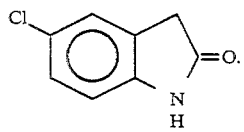

The process includes in a first step, convening chloronitrobenzene of the formula:

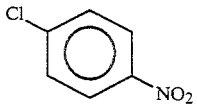

with a chloroacetic acid alkyl ester of the general formula:

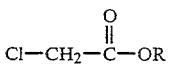

wherein R means a $C_1$–$C_7$-alkyl group, branched or unbranched, in the presence of a base to a chloronitrobenzene acetic acid alkyl ester of the general formula:

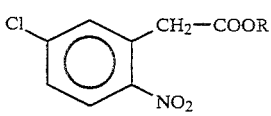

wherein R has the above-mentioned meaning. The latter is catalytically hydrogenated in a second step with hydrogen to the corresponding amine of the general formula:

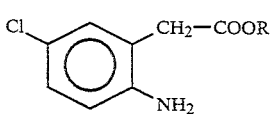

wherein R has the above-mentioned meaning. The amine is then cyclized in a third step to the end product according to formula I in the presence of an acid.

5-Chloroxindole is an important intermediate product for the production of pharmaceutical agents, such as, for the production of 1,3-disubstituted 2-oxoindoles (U.S. Pat. No. 4,721,712).

The invention also involves a process for the production of chloronitrobenzene acetic acid alkyl esters of the general formula:

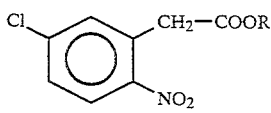

wherein R has the above-mentioned meaning. The process includes reacting chloronitrobenzene of the formula:

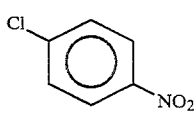

with a chloro-acetic acid alkyl ester of the general formula:

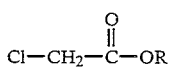

wherein R has the above-mentioned meaning, in the presence of an alkali amide in liquid ammonia.

DETAILED DESCRIPTION OF THE INVENTION

According to the invention the process for the production of 5-chloroxindole of the formula:

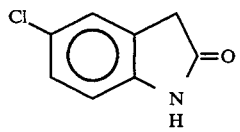

is performed so that, in the first step, chloronitrobenzene of the formula:

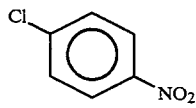

is converted with a chloroacetic acid alkyl ester of the general formula:

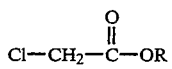

wherein R means a $C_1$-$C_7$-alkyl group, branched or unbranched, in the presence of a base to a chloronitrobenzene acetic acid alkyl ester of the general formula:

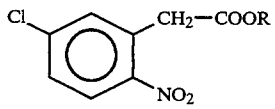

wherein R has the above-mentioned meaning. The latter is catalytically hydrogenated in the second step with hydrogen to the corresponding amine of the general formula:

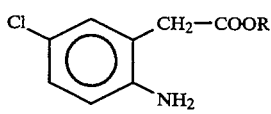

wherein R has the above-mentioned meaning. Then the latter is cyclized in the third step in the presence of an acid to the end product according to formula I.

The first step is performed with chloronitrobenzene of formula II and with a chloroacetic acid-$C_1$-$C_7$-alkyl ester of general formula III. As suitable representatives of the chloroacetic acid-$C_1$-$C_7$-alkyl ester are those in which $C_1C_7$ means a methyl, ethyl, propyl, isopropyl, tertiary butyl or tertiary pentyl group. Preferably $C_1$-$C_7$ therein means an ethyl group. Preferably the chloroacetic acid-$C_1$-$C_7$-alkyl ester is used in excess relative to chloronitrobenzene, preferably in an amount of 1.3 to 1.7 mol relative to 1 mol of chloronitrobenzene.

As a solvent of these two reactants, nonpolar solvents, for example, toluene, diethylether, tetrahydrofuran and tertiary butylmethyl ether, can be used. Preferably toluene is used as the nonpolar solvent. The first step is performed in the presence of a base. As the base, for example, alkali amides and alkali hydroxides can be used. As the alkali hydroxide, for example, sodium hydroxide or potassium hydroxide is used. As the alkali amide, for example, sodium amide or potassium amide is used. Suitably as the base, an alkali amide in liquid ammonia is used; preferably sodium amide, which is formed particularly in situ from the corresponding elementary metal in liquid ammonia, optionally in the presence of a catalyst, is used.

In an especially preferred embodiment of the first step the alkali amide formed in situ in the presence of an alcohol of the general formula:

  R—OH  VI wherein R has the above-mentioned meaning, is used. Suitable as representatives of these alcohols are those wherein R means methyl, ethyl, propyl, isopropyl, tertiary butyl or tertiary pentyl, preferably tertiary butyl. Preferably the alcohol and the alkali amide are used equimolar.

Suitably the reaction is performed in the first step at a temperature of −30° to −40° C.

After a usual reaction time of 0.1 to 2 hours, the chloronitrobenzene acetic acid alkyl ester according to the formula:

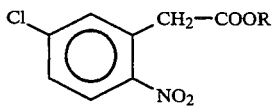

wherein R has the above-mentioned meaning, can be isolated by addition of ammonium chloride in ways usual to one skilled in the art.

In the second step, the hydrogenation of the chloronitrobenzene acetic acid alkyl ester (formula IV) to the corresponding amine (formula V), is catalytically performed with hydrogen. As the hydrogenation catalyst, noble metal, noble metal oxide or Raney catalysts, optionally applied on a suitable vehicle (support), can be used. For example, Raney nickel or platinum on carbon can be used as hydrogenation catalyst.

Suitably platinum on carbon, especially 0.5 to 5 percent by weight of platinum on carbon, is used as the hydrogenation catalyst. The hydrogenation catalysts can be used in an amount of 0.1 to 20 percent by weight, preferably 5 to 10 percent by weight, relative to the chloronitrobenzene acetic acid alkyl ester.

Suitably the hydrogenation takes place at an elevated $H_2$ pressure, preferably at a pressure of 5 to 10 bar. Suitably the second stage is performed in a nonpolar solvent, such as, toluene, or in a polar solvent, such as, alcohols or esters. As the ester solvent, for example, acetic acid methyl or ethyl acetate can be used. As the alcohol solvents, for example, methanol, ethanol or propanol, preferably ethanol, can be used. Suitably the reaction in the second step is performed at a temperature of 0° to 55° C., preferably 10° to 20° C.

After a usual reaction time of 1 to 20 hours, the amine (formula V) can then be isolated either according to methods usual to one skilled in the art or after separation of the catalyst, used directly for the third step. Preferably the amine, without isolation, is used directly for the third step.

In the third step the amine of general formula V is cyclized in the presence of an acid to 5-chloroxindole (formula I). As the acid, for example, toluene-4-sulfonic acid, methane sulfonic acid or their hydrates can be used. Preferably toluene-4-sulfonic acid or its hydrates are used as the acid.

Suitably the acid is used in an amount of 0.0005 to 0.1 mol, preferably of 0.05 to 0.1 mol, per mol of amine. As the solvent for the third step, those described for the second step can be used. The reaction in the third step suitably takes place at a temperature from 50° C. up to the reflux temperature, preferably from 70° C. up to the reflux temperature of the solvent.

After a usual reaction time of 1 to 20 hours, 5-chloroxindole can be isolated in good yields according to methods usual to one skilled in the art.

EXAMPLE

Production of 5-chloroindole (a) Production of chloronitrobenzene acetic acid alkyl ester (First step)

250 ml of NH₃ was condensed in a flask which had been dried and flushed with argon (cryometer temperature −40° C). A small piece of sodium was added—blue solution. After addition of 250 mg of iron (III) nitrate-nonahydrate, the solution decolorized. Within 15 minutes, 5.75 g (250 mmol) of sodium was added in small pieces. It was then stirred for 10 minutes. Then 18.53 g (250 mmol) of tertiary butanol, dissolved in 3 ml of toluene, was instilled for 15 minutes and stirred for 35 minutes—a grey suspension resulted. Immediately after this, a mixture of 15.76 g (100 mmol) of 4-chloronitrobenzene and 18.38 g (150mmol) of chloroacetic acid ethyl ester, dissolved in 20 ml of toluene, was instilled for 15 minutes (reaction mixture turned blue). It was restirred for one hour after the addition; then 26.75 g (500 mmol) of solid ammonium chloride was carefully added. Then the dry-ice cooler was removed and the suspension heated within about 30 minutes to 10° C. (removal of NH₃). Then, within 20 minutes, 200 ml of toluene was instilled (cryometer temperature: 10° C.). After 30 minutes the reaction mixture was filtered on a G3-glass suction filter (with Celite). The filtrate was concentrated by evaporation on a rotary evaporator at 35° C. and at 25 mbar and dried on a high vacuum for about 30 minutes. 27.14 g of product, content (HPLC): 78.8 percent, corresponding to a yield of 87.8 percent, relative to the feedstock used, was obtained.

(b) Production of chlorobonitrobenzen amide ethyl acetate (Second Step)

26.73 g of crude product from the first step was dissolved in 135 ml of ethanol at room temperature. After addition of 1.0 g of Pt/C the autoclave was flushed three times with H₂ and then bars of H₂ was pressed on and stirred for 7.5 hours at room temperature. Then the reaction mixture was filtered off and the filter residue washed with 25 ml of ethanol. The filter solution thus obtained was directly further processed (third step).

(c) Production of chloroxindole (Third Step)

The filter solution of the second step was mixed with 1.90 g (10 mmol) of toluene-4-sulfonic acid-monohydrate, and then refluxed for 30 minutes. A total of 125 ml of ethanol was then distilled off during 4.5 hours, whereupon a suspension developed. The reaction mixture was cooled to room temperature and filtered. The filter residue was washed with a total of 60 ml of ethanol (3×20 ml portions) and then dried for 12 hours at 35° C. and at 40 mbar. 12.07 g of rose-violet solid was obtained as product, content (HPLC): 94.3 percent corresponding to a yield of 67.9 percent, relative to the chloronitrobenzene used (first step).

What is claimed is:

1. The process for the production of a chloronitrobenzene acetic acid alkyl ester of formula:

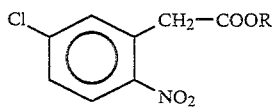
IV wherein R is a C₁-C₇-alkyl group, branched or unbranched, comprising reacting chloronitrobenzene of formula:

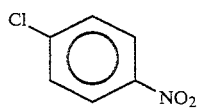
II with a chloro acetic acid alkyl ester of formula:

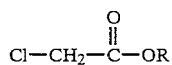
III wherein R has the above-mentioned meaning, in the presence of an alkali amide in liquid ammonia.

2. The process according to claim 1 wherein the reaction is performed in the presence of an alcohol of formula:

R—OH    VI wherein R has the above-mentioned meaning.

3. The process according to claim 2 wherein tertiary butanol is used as the alcohol and sodium amide is used as the alkali amide.

4. The process according to claim 3 wherein the reaction is performed at a temperature of −30° to −40° C.

5. The process according to claim 1 wherein sodium amide is used as the alkali amide.

6. The process according to claim 1 wherein the reaction is performed at a temperature of −30° to −40° C.

* * * * *